(12) United States Patent
Nowak et al.

(10) Patent No.: US 8,758,729 B2
(45) Date of Patent: Jun. 24, 2014

(54) ORAL COMPOSITIONS CONTAINING POLYGUANIDINIUM COMPOUNDS AND METHODS OF MANUFACTURE AND USE THEREOF

(75) Inventors: Andrew Nowak, Los Angeles, CA (US); Shira Pilch, Highland Park, NJ (US); Jim Masters, Ringoes, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 13/266,930

(22) PCT Filed: May 18, 2009

(86) PCT No.: PCT/US2009/044349
§ 371 (c)(1),
(2), (4) Date: Oct. 28, 2011

(87) PCT Pub. No.: WO2010/134904
PCT Pub. Date: Nov. 25, 2010

(65) Prior Publication Data
US 2012/0045400 A1    Feb. 23, 2012

(51) Int. Cl.
| | | |
|---|---|---|
| A61Q 11/00 | (2006.01) | |
| A61K 6/00 | (2006.01) | |
| A61K 8/00 | (2006.01) | |
| A61K 8/02 | (2006.01) | |
| A61K 8/24 | (2006.01) | |
| A61K 8/25 | (2006.01) | |
| A61K 8/43 | (2006.01) | |

(52) U.S. Cl.
USPC ............. 424/49; 424/401; 424/488; 424/54; 424/57; 424/602; 433/215; 433/216; 433/217.1

(58) Field of Classification Search
USPC ............. 424/49, 401, 488, 54, 57, 601, 602; 433/215, 216, 217.1
See application file for complete search history.

(56) References Cited

U.S. PATENT DOCUMENTS

| | | |
|---|---|---|
| 3,538,230 A | 11/1970 | Pader et al. |
| 3,956,480 A | 5/1976 | Dichter et al. |
| 3,966,863 A | 6/1976 | Forward et al. |
| 3,980,767 A | 9/1976 | Chown et al. |
| 3,996,863 A | 12/1976 | Osborn |
| 4,110,083 A | 8/1978 | Benedict |
| 4,138,477 A | 2/1979 | Gaffar |
| 4,138,914 A | 2/1979 | Reeder |
| 4,198,394 A | 4/1980 | Faunce |
| 4,314,990 A | 2/1982 | Denny, Jr. et al. |
| 4,328,205 A | 5/1982 | Taylor |
| 4,358,437 A | 11/1982 | Duke |
| 4,373,036 A | 2/1983 | Chang et al. |
| 4,485,090 A | 11/1984 | Chang |
| 4,521,551 A | 6/1985 | Chang et al. |
| 4,532,124 A | 7/1985 | Pearce |
| 4,634,589 A | 1/1987 | Scheller |
| 4,853,367 A | 8/1989 | Henzel et al. |
| 4,992,258 A | 2/1991 | Mason |
| 5,028,413 A | 7/1991 | Bianchi et al. |
| 5,032,178 A | 7/1991 | Cornell |
| 5,188,821 A | 2/1993 | Gaffar |
| 5,192,531 A | 3/1993 | Gaffar et al. |
| 5,240,697 A | 8/1993 | Norfleet et al. |
| 5,310,543 A | 5/1994 | Dawson |
| 5,352,439 A | 10/1994 | Norfleet et al. |
| 5,354,550 A | 10/1994 | Collins et al. |
| 5,505,933 A | 4/1996 | Norfleet et al. |
| 5,603,922 A | 2/1997 | Winston et al. |
| 5,605,677 A | 2/1997 | Schumann et al. |
| 5,624,652 A | 4/1997 | Aldcroft et al. |
| 5,629,282 A * | 5/1997 | Bhakoo .................. 514/2.4 |
| 5,645,853 A | 7/1997 | Winston et al. |
| 5,723,105 A | 3/1998 | Viscio et al. |
| 5,833,957 A | 11/1998 | Winston et al. |
| 5,876,701 A | 3/1999 | Wong et al. |
| 5,939,051 A | 8/1999 | Santalucia et al. |
| 6,036,944 A | 3/2000 | Winston et al. |
| 6,117,415 A | 9/2000 | Schwarz |
| 6,214,321 B1 | 4/2001 | Lee et al. |
| 6,217,851 B1 | 4/2001 | Kleinberg et al. |
| 6,241,972 B1 | 6/2001 | Herms et al. |
| 6,248,310 B1 | 6/2001 | Lee et al. |
| 6,294,163 B1 | 9/2001 | Dhal et al. |
| 6,447,756 B1 | 9/2002 | Dixit et al. |
| 6,524,558 B2 | 2/2003 | Kleinberg et al. |

(Continued)

FOREIGN PATENT DOCUMENTS

| | | |
|---|---|---|
| EP | 0102200 | 3/1984 |
| EP | 0467548 | 1/1992 |

(Continued)

OTHER PUBLICATIONS

Amaechi et al., 2005, "Dental Erosion: Possible Approaches to Prevention and Control," J. Dentistry 33(3):243-252.
Anonymous, 2007, "Sensodyne Pronamel Toothpaste Sensodyne Enamel-Pro Toothpaste," Safeguarding Public Health, MHRA.
International Search Report and Written Opinion in International Application No. PCT/US10/060970, mailed May 31, 2012.
Acevedo et al., 2005, "The Inhibitory Effect of an Arginine Bicarbonate/Calcium Carbonate (CaviStat®)-Containing Dentifrice on the Development of Dental Caries in Venezuelan School Children," J. Clin. Dent. 16:63-70.

(Continued)

*Primary Examiner* — Lezah Roberts
(74) *Attorney, Agent, or Firm* — Howard C. Lee (57) ABSTRACT

The invention describes the modification of polyamine-based materials to form polyguanidine compounds that are useful for their antimicrobial, anticaries, and muccoadhesive properties. The present invention also relates to methods for preventing or treating periodontal disease and caries which include delivering a therapeutically effective amount of an oral composition containing a polyguanidine compound into an oral cavity.

17 Claims, 3 Drawing Sheets

(56) References Cited

U.S. PATENT DOCUMENTS

| | | | |
|---|---|---|---|
| 6,790,460 | B2 | 9/2004 | Shefer et al. |
| 6,936,640 | B2 | 8/2005 | McQueen et al. |
| 6,953,817 | B2 | 10/2005 | Fisher et al. |
| 7,018,625 | B2 | 3/2006 | Ulmer et al. |
| 7,402,416 | B2 | 7/2008 | Szeles et al. |
| 7,435,409 | B2 | 10/2008 | Nelson et al. |
| 2002/0037258 | A1 | 3/2002 | Dodd et al. |
| 2002/0064504 | A1* | 5/2002 | Kleinberg et al. ............ 424/49 |
| 2003/0026768 | A1 | 2/2003 | Yu et al. |
| 2004/0126335 | A1 | 7/2004 | Faller et al. |
| 2004/0241108 | A1 | 12/2004 | Stanier et al. |
| 2005/0129628 | A1 | 6/2005 | Stanier et al. |
| 2005/0186288 | A1 | 8/2005 | Chiou et al. |
| 2005/0196358 | A1 | 9/2005 | Georgiades et al. |
| 2005/0281757 | A1 | 12/2005 | Ibrahim et al. |
| 2006/0008423 | A1 | 1/2006 | Araya et al. |
| 2006/0024246 | A1 | 2/2006 | Maitra et al. |
| 2006/0039957 | A1 | 2/2006 | Krumme |
| 2006/0045851 | A1 | 3/2006 | Fitzgerald et al. |
| 2006/0045855 | A1 | 3/2006 | Sasson |
| 2006/0093563 | A1 | 5/2006 | Segura et al. |
| 2006/0251737 | A1 | 11/2006 | Dutra Zanotto et al. |
| 2007/0014741 | A1 | 1/2007 | Chiu |
| 2007/0104660 | A1 | 5/2007 | Miksa et al. |
| 2007/0258916 | A1* | 11/2007 | Ferracane et al. ............ 424/57 |
| 2007/0264291 | A1 | 11/2007 | Greenspan et al. |
| 2008/0226566 | A1 | 9/2008 | Poth et al. |
| 2008/0267891 | A1 | 10/2008 | Zaidel et al. |
| 2008/0268001 | A1 | 10/2008 | Zaidel et al. |
| 2008/0274065 | A1* | 11/2008 | Robinson et al. ............ 424/52 |
| 2009/0068259 | A1 | 3/2009 | Pilch et al. |
| 2009/0105262 | A1 | 4/2009 | Whiteford |
| 2010/0093661 | A1 | 4/2010 | Badwan et al. |
| 2012/0045400 | A1 | 2/2012 | Nowak et al. |

FOREIGN PATENT DOCUMENTS

| | | |
|---|---|---|
| EP | 0480812 | 4/1992 |
| EP | 0845976 | 6/1998 |
| EP | 1260482 | 11/2002 |
| GB | 702268 | 1/1954 |
| GB | 1598233 | 9/1981 |
| RU | 2085184 | 7/1997 |
| RU | 2324478 | 5/2008 |
| WO | WO 93/07851 | 4/1993 |
| WO | WO 97/32565 | 9/1997 |
| WO | WO 00/16712 | 3/2000 |
| WO | WO 00/78270 | 12/2000 |
| WO | WO 01/70178 | 9/2001 |
| WO | WO 2004/032674 | 4/2004 |
| WO | WO 2005/063185 | 7/2005 |
| WO | WO 2007/051546 | 5/2007 |
| WO | WO 2009/009814 | 1/2009 |
| WO | WO 2009/032404 | 3/2009 |
| WO | WO 2010/041073 | 4/2010 |

OTHER PUBLICATIONS

Ariely et al., 1966, "Synthesis of Poly-L-Arginine," Biopolymers 4(1):91-96.

Cunin et al., 1986, "Biosynthesis and Metabolism of Arginine in Bacteria," Microbiological Reviews, 50(3):314-352.

Hefferren: 1976, "A Laboratory Method for Assessment of Dentifrice Abrasivity," J. Dent. Res. 55(4):563-573.

International Search Report and Written Opinion in International Application No. PCT/US08/061925, mailed Feb. 5, 2010.

International Search Report and Written Opinion in International Application No. PCT/US09/044349, mailed Dec. 8, 2009.

International Search Report and Written Opinion in International Application No. PCT/US10/021582, mailed Aug. 9, 2011.

Jal et al., 2004, "Chemical modification of silica surface by immobilization of functional groups for extractive concentration of metal ions," Talanta 62(5):1005-1028.

Johnson et al., 2006, "Oral Health and General Health," Advances in Dental Research 19:118-121.

McConnell et al., 2009, "Bacterial plaque retention on oral hard materials: Effect of surface roughness, surface composition, and physisorbed polycarboxylate," J. Biomedical Materials Research Part A 92(4):1518-1527.

Pashley et al., 1984, "Effects of Desensitizing Dentifrices in vitro," J. Periodontology 55(9)522-525.

Pashley et al., 1993, "The Effects of Outward Forced Convective Flow on Inward Diffusion in Human Dentine in vitro," Arch. Oral Biol. 38(7):577-582.

Pashley et al., 2002, "The Effects of Outward Forced Convective Flow on Inward Diffusion of Potassium across Human Dentin," American J. of Dentistry, Medline Database Accession No. NLM12572645, Abstract.

Sakai et al., 2003, "Anion-Mediated Transfer of Polyarginine Across Liquid and Bilayer Membranes," J. Am. Chem. Soc. 125(47):14348-14356.

Stober et al., 1968, "Controlled Growth of Monodisperse Silica Spheres in the Micron Size Range," J. Colloid and Interface Science 26:62-69.

Zhang et al., 1998. "The Effects of Pain-Free Desensitizer on Dentine Permability and Tubule Occlusion over Time, in vitro," J. Clinical Periodontology 25(11 Pt. 1):884-891.

Du et al., 2008, "Clinical evaluation of a dentifrice containing calcium sodium phosphosilicate (novamin) for the treatment of dentin hypersensitivity," American J. Dentistry 21(4):210-214.

* cited by examiner

Fig. 3

# ORAL COMPOSITIONS CONTAINING POLYGUANIDINIUM COMPOUNDS AND METHODS OF MANUFACTURE AND USE THEREOF

CROSS-REFERENCE TO RELATED APPLICATIONS

The present application is a national stage entry under 35 U.S.C. §371 of International Patent Application No. PCT/US2009/044349, filed May 18, 2009, the entirety of which is hereby incorporated by reference.

FIELD OF THE INVENTION

The invention encompasses oral care compositions including a polyguanidine compound distributed in an orally acceptable carrier. The invention also encompasses methods for preparing oral compositions containing a polyguanidine compound and methods of use thereof. Methods for targeting an active ingredient to oral epithelial tissues, depositing a bacteriostatic or bacteriocidal material on oral surfaces, retarding or preventing dental caries, treating or preventing dentinal sensitivity, plugging dentinal tubules, treating a carious lesion, calcifying an exposed tooth pulp, and calcifying the base or all of a pit or fissure in a tooth, and the like, are also encompassed by the invention, which include delivering a therapeutically effective amount of an oral composition including a polyguanidine compound into the oral cavity.

BACKGROUND OF THE INVENTION

Periodontal disease and caries are the most prevalent dental problems. Aside from affecting oral tissues, periodontal disease has also been associated with various systemic diseases. Gingivitis, the mild form of the disease, is characterized by host tissue inflammation and bacterial plaque accumulation around the gingival margin. Treatment of gingivitis by improved oral hygiene practices can significantly reverse the disease condition. However, left untreated, gingivitis can lead to the more serious and irreversible periodontitis, which involves progressive loss of the alveolar bone around the teeth, and if left untreated, can lead to the loosening and subsequent loss of teeth.

Caries is among the most infectious dental diseases and may result in demineralization and loss of enamel, dentine, and cementum. Untreated, bacterial plaques causing caries may also lead to dentinal hypersensitivity and pain, and subsequent loss of teeth. Acids produced as end-products of the bacterial degradation of fermentable carbohydrates dissolve hydroxyapatite, a calcium phosphate mineral that comprises most of the mineral of the enamel, dentine, and cementum. Acidic agents, including certain foods and oral personal care products may also cause tooth demineralization. Among the latter are many of the commercially available mouthwashes and abrasive toothpastes.

SUMMARY OF THE INVENTION

The invention encompasses compositions including polyamine-based materials, which form polyguanidine compounds that are useful for their antimicrobial, anticaries, and muccoadhesive properties. Accordingly, the invention encompasses polyguanidine compounds that include active ingredients with antimicrobial and acid neutralizing properties to target bacterial plaques associated with, for example, periodontal disease and caries on oral cavities.

In one embodiment, the invention encompasses an oral composition containing a polyguanidine compound including a counterion and an orally acceptable carrier.

In another embodiment, the invention encompasses methods for preparing an oral composition including a polyguanidine compound including a counterion distributed in an orally acceptable carrier.

In another embodiment, the invention encompasses methods of inhibiting bacterial plaque in the oral cavity by contacting the oral epithelial tissues and/or teeth of a mammal with a composition including a therapeutically effective amount of a polyguanidine compound including a counterion.

In another embodiment, the invention encompasses methods of preventing the onset of periodontal disease and caries on oral cavities by contacting the oral epithelial tissues and/or teeth of a mammal with a composition including a therapeutically effective amount of a polyguanidine compound including a counterion.

In another embodiment, the invention encompasses methods of depositing a bacteriostatic or bacteriocidal material on oral surfaces, that persists after brushing or rinsing, including delivering an oral composition including a therapeutically effective amount of a polyguanidine compound including a counterion into an oral cavity.

In another embodiment, the invention encompasses methods of retarding or preventing dental caries including delivering a therapeutically effective amount of an oral composition containing a polyguanidine compound including a counterion into an oral cavity.

In another embodiment, the invention encompasses methods of treating or preventing dentinal sensitivity including delivering a therapeutically effective amount of an oral composition containing a polyguanidine compound including a counterion into an oral cavity.

In another embodiment, the invention encompasses methods of occluding dentinal tubules including delivering a therapeutically effective amount of an oral composition containing a polyguanidine compound including a counterion into an oral cavity.

In another embodiment, the invention encompasses methods of treating a carious lesion including delivering a therapeutically effective amount of an oral composition containing a polyguanidine compound including a counterion into an oral cavity.

In another embodiment, the invention encompasses methods of calcifying an exposed tooth pulp including delivering a therapeutically effective amount of an oral composition containing a polyguanidine compound including a counterion into an oral cavity.

In another embodiment, the invention encompasses methods of calcifying the base or all of a pit or fissure in a tooth including delivering a therapeutically effective amount of an oral composition containing a polyguanidine compound including a counterion into an oral cavity.

DETAILED DESCRIPTION OF THE INVENTION

The invention encompasses oral care compositions including a polyguanidine compound or a salt thereof and an orally acceptable carrier and methods for preparing the same. The invention also encompasses methods for preventing or treating periodontal disease and caries, which include delivering an oral composition including a therapeutically effective amount of a polyguanidine compound or a salt thereof into the oral cavity.

I. Polyguanidine Compositions

The invention encompasses oral care compositions including at least one polyguanidine compound or a salt thereof that is useful for its antimicrobial, anticaries, and/or muccoadhesive properties. The polyguanidine compounds and salts thereof included in the invention allow the deposition of the therapeutic agents and counterions onto oral surfaces, act as antimicrobial agents to inhibit the growth of bacterial species long after use of the composition, and maintain an elevated pH and promote remineralization. In some embodiments, polyguanidine compositions of the present invention include: at least one polycation species, at least one counterion species, and at least one orally acceptable carrier.

A. Poly(Guanidinium) Compounds of the Invention

The invention encompasses oral compositions including at least one polyguanidinium compound. As used herein, the term "polyguanidine" or "polyguanidinium" are used interchangeably and refers to compounds of Formula (I):

(I)

wherein $R_1$ is hydrogen, hydroxide, methoxide, and linear or branched, saturated or unsaturated, optionally hydroxylated $C_1$ to $C_{16}$ alkyl groups when Z is CH or hydrogen and linear or branched, saturated or unsaturated, optionally hydroxylated $C_1$ to $C_{16}$ alkyl when Z is N;

$R_2$ and $R_3$ are each independently hydrogen or linear or branched, saturated or unsaturated, optionally hydroxylated $C_1$ to $C_{16}$ alkyl groups A is a covalent bond or linear or branched, saturated or unsaturated, optionally hydroxylated $C_1$ to $C_{16}$ alkyl groups;

Z is a CH or N;

X— is a counter ion, for example, bicarbonate or chloride; and n is an integer between 2 and 5,000.

The polyguanidinium compounds of the invention can exist an orally acceptable poly-charged ion or salt capable of disassociation into poly-charged ions, with a net positive charge. In some embodiments, the polycation species is a polyamine. In some embodiments, the polycation species is a polyguanidinium compound.

In some embodiments, the polyguanidine compound includes at least one side group ($R_1$). In some embodiments, the side group ($R_1$) is hydrogen; hydroxyl; and linear or branched, saturated or unsaturated, optionally hydroxylated $C_1$ to $C_{16}$ alkyl groups. In one embodiment, the side group is a hydrogen atom.

In some embodiments, the polyguanidine compound includes a carbohydrate chain (A). In some embodiments, the alkyl chain (A) is linear or branched, saturated or unsaturated, optionally hydroxylated $C_1$ to $C_{16}$ alkyl groups. In some embodiments, the alkyl chain (A) is linear or branched, saturated or unsaturated, $C_1$ to $C_{16}$ alkylene radicals optionally substituted with at least one group including: hydroxyl, carboxyl, or carboxylate radicals or halogens; the alkylene radicals optionally containing at least one function group selected from the group consisting of: amines, ethers, thioethers, esters, amides, carbamates, urea, $C_6$ aryl or $C_3$ to $C_8$ rings optionally substituted with $C_1$-$C_8$ alkyl groups, hydroxyls or halogens. In some embodiments, the alkyl chain (A) is one or more $C_6$ or $C_7$ aryl or $C_5$ to $C_7$ cyclanyl rings unsubstituted or substituted with a $C_1$-$C_8$ alkyl, a hydroxyl group or a halogen. In some embodiments, the carbohydrate chain (A) is selected from the group consisting of: a $C_{10}$ to $C_{14}$ polyaryl or $C_6$ to $C_{10}$ polycyclanyl chains, which may be interrupted with at least one function group selected from the group consisting of: a $C_1$ to $C_8$ alkylene radical, amine, amide, ether, thioether, hydrogen atom, carbamate or urea.

In some embodiments, the polyguanidine compound includes n units, where n denotes an integer between 2 and 5,000.

In certain embodiments, the polyguanidinium compound is:

101

102

103

In some embodiments, the polyguanidine compound has antimicrobial properties. In one embodiment, the antimicrobial activity of the polyguanidine compounds is due the presence of strongly basic cationic structures—analogous to chlorhexidine. Without being limited by theory, the mechanism of action is due to the positive charge, which is strongly attracted to acidic groups found in salivary proteins. As a result, it binds strongly to pellicle and soft tissues in the oral cavity where it can reside over several hours. Accordingly, the polyguanidinium salts inhibit bacterial growth in the oral cavity through adhesion to the negatively charged bacterial wall and subsequent disruption of $Ca^{2+}$ salt bridges necessary for bacterial plaque adhesion to the pellicle and gingiva. In one embodiment, the polyguanidine compounds of the invention are polycations that have general antimicrobial activity due to their affinity for the negatively charged bacterial cell wall. In one embodiment, this opposite charged interaction causes association with and disruption of the bacterial membrane than can lead to inhibition of bacterial plaque adhesion or bacterial cell death.

In some embodiments, the polyguanidinium compounds of the invention has muccoadhesive properties. In some embodiments, these muccoadhesive properties include electrostatic and lipophilic interactions. Oral surfaces, including mucosal epithelium, have a net negative charge due to membrane glycoproteins and glycolipids. Glycoproteins in saliva also contain overall negative charges. In addition, oral surfaces contain large numbers of phosphate and bidentate charged species embedded in the cell membrane that may interact with polycations to create a strongly adhesive lipophilic moiety that may traverse the cell lipid membrane. Accordingly, in one embodiment, the polyguanidinium compounds of the invention have a strong affinity to oral mucosal surfaces due to electrostatic interactions.

In one embodiment, the polyguanidinium compounds form strongly adhesive lipophilic moieties that may be adsorbed into oral tissues. In one embodiment, the polyguanidine compounds target associated active ingredients directly to an oral surface. In one embodiment, the polyguanidine compounds facilitate adsorption of the active ingredients into oral tissues. In one embodiment, the active ingredients are selected from the group consisting of bacteriostatic and bacteriocidal materials. In one embodiment, the polyguanidine compounds deposit bacteriostatic or bacteriocidal materials on the oral surfaces that persist long after brushing and rinsing.

B. Counterions

In some embodiments, the oral care composition of the invention includes at least one counterion species. In some embodiments, a source of the counterions is selected from the group consisting of: antimicrobials, anti-caries agents, and acid-neutralizing compounds. In some embodiments, an oral composition of the present invention incorporates counterions selected from the group consisting of: carbonates and phosphates. In some embodiments, the counterion species is a carbonate. In some embodiments, the counterion species is a bicarbonate. In some embodiments, the counterion species is a phosphate. In some embodiments, the counterion species is a chloride.

In one embodiment, the at least one counterion species is bicarbonate. In some embodiments, an oral composition of the invention further includes a second counterion species. In some embodiments, the second counterion species is a carbonate. In one embodiment, the second counterion species is calcium carbonate.

In some embodiments, an oral composition of the invention includes a counterion species that can neutralize acids and/or affect the metabolism of bacteria found on oral surfaces. In some embodiments, the counterion species may reduce demineralization. In some embodiments, the counterion species is a phosphate that may reduce tooth demineralization by providing a surface poison on the tooth enamel and by hydrolyzing to orthophosphate which suppresses the solubilization of tooth enamel by mass action.

In some embodiments, the counterion species is a carbonate or bicarbonate that provides buffering that reduces the amount of acid in dental plaque and on the tooth surface available for dissolution of tooth mineral. In some embodiments, the carbonate or bicarbonate counterion species enhances the acid neutralizing activity of the polyguanidine compound by maintaining the pH near the optimum pH for the degradation of guanidine by the plaque bacteria. Guanidine is metabolized by many bacteria as a source of nitrogen compounds. Its breakdown results in the production of ammonia as a byproduct which also contribute to acid neutralization and the maintenance of higher pH levels. In some embodiments, the carbonate or bicarbonate counterion species maintains the pH to levels from pH 6.0 to pH 9.0. In one embodiment, the pH of the oral composition ranges from pH 7.0 to pH 8.0. In some embodiments, the carbonate or bicarbonate counterion species reduces the concentration of carbon dioxide when acid is neutralized.

C. Carriers

Acceptable oral carriers include any conventional oral delivery system, such as dental care products, food products, and chewing gum. Examples of dental care products may include, but are not limited to, dentifrices, topical solutions or pastes, mouthwashes in the form of liquids or sprays or slurries, powders, gels or tablets, and dental flosses. Examples of food products which may contain oral compositions described herein include, but are not limited to, lozenges and confections.

In some embodiments, oral compositions of the present invention may contain any conventional ingredient for the particular oral carrier as known to one of ordinary skill in the art. For example, liquid mouthwashes may contain a solvent such as distilled or deionized water, ethanol and the like; a sweetening agent such as saccharine, aspartame and the like;

and a flavoring agent such as peppermint oil, spearmint oil and the like. Dentifrice pastes or gels may contain, for example, water, glycerine or sorbitol, a conventional abrasive such as calcium pyrophosphate, aluminum hydroxide, resins, insoluble alkali metal metaphosphates and the like; a binder such as hydroxyethyl cellulose, xanthin gum, sodium carboxymethyl cellulose and the like; a foaming agent such as sodium lauryl sulfate, sodium coconut monoglyceride sulfonate, sodium-N-methyl-N-palmitoyl tauride and the like; a flavoring agent; a sweetening agent; an antiseptic agent and any other ingredient required for the particular formulation. Dentifrice powders may contain a conventional abrasive and a flavoring agent. Tablets and powders may contain, for example, a vehicle such as lactose, mannitol and the like; a binder such as corn starch, carboxymethyl cellulose and the like; and a disintegrator.

A dentifrice or paste for localized application to a sensitive tooth site such as breeched cementum of an orally exposed root surface may be one that is simpler in composition and applied with a soft applicator. Such a dentifrice or paste may or may not contain conventional abrasive, foaming agent, and flavoring agents. Localized sites such as the dentine following tooth preparation for a dental restoration would also involve simpler compositions and include fillers used in dental pulp cappings, cavity liners and cements and any other ingredients required for the composition by those skilled in the art. For example, zinc oxide and eugenol may be appropriate for dental cement compositions.

D. Excipients

In some embodiments, a polyguanidine composition of the invention may further include at least one excipient. The excipient may be selected from any chemical group or class of compounds suitable for use in the invention.

In some embodiments, an oral composition of the present invention further includes a calcium salt. In some embodiments, the calcium salt is selected from the group consisting of: calcium carbonate, monocalcium phosphate, dicalcium phosphate, tricalcium phosphate, calcium fluoride, clacium monofluorophosphate, sodium calcium pyrophosphate, calcium laurate, calcium palmitate, and combinations thereof. In one embodiment, the calcium salt is calcium carbonate. In some embodiments, the calcium salt produces calcium hydroxide to remineralize the dental enamel. In some embodiments, the calcium salt is calcium fluoride. In some embodiments, an oral composition of the present invention includes a therapeutically effective amount of calcium fluoride.

In some embodiments, an oral composition of the present invention further includes a phosphorous source. In some embodiments, the phosphorous source is a phytate or phytic acid selected from the group consisting of: inositol triphosphate (IP3), inositol tetraphosphate (IP4), inositol pentaphosphate (IP5), inositol hexakisphosphate (IP6), and combinations thereof. These compounds contain multiple phosphate groups and as a result are able to form ionic bridges with cations.

In some embodiments, an oral composition of the present invention including a polyguanidine compound and a bicarbonate counterion species further includes calcium carbonate and a phytate salt. In some embodiments, said oral composition including a polyguanidine compound and a bicarbonate counterion species, and further including calcium carbonate and a phytate salt is able to prevent pH fall through the buffering capability of the bicarbonate and carbonate ions. The polyguanidine compound of the present invention is able to carry multiple bicarbonate counterions per chain for acid neutralization. The large pKa value of the guanidinium groups first allows them to stabilize the bicarbonate counterion species. Bicarbonate and carbonate are then able to directly react with and neutralize acidic byproducts from carbohydrate fermentation products produced by bacterial plaques. This elevated pH range inhibits the formation of caries and promotes remineralization through the presence of calcium ions.

In some embodiments, the polyguanidine compound, calcium carbonate, and phytate salt may also interact to form a complex compound. In some embodiments, the polyguanidine compound and calcium carbonate may bind to the phytate salt to form a calcium guanidine phytate complex. In some embodiments, the incorporation and delivery of $Ca^{2+}$ ions into the polyguanidine-based oral composition of the present invention is aided by the use of a phytate salt, which forms ionic bridges between the $Ca^{2+}$ and guanidinium polycations.

II. Other Ingredients in the Compositions of the Invention

In certain embodiments, the invention may include any another additive conventionally used in dentifrice formulations. Any suitable additive in any suitable amount or form may be used. Suitable additives for use in the invention include, but are not limited to: surfactants, desensitizing agents including potassium salts, fluorine sources, whitening agents, tartar control agents, antibacterial agents, abrasives including silica, binders and thickening agents, detergents, adhesion agents, foam modulators, pH modifying agents, mouth-feel agents, sweeteners, flavorants, colorants, preservatives, combinations thereof, and the like. It is to be understood that these additives are optional components and can be, individually or collectively, excluded from the automatic dishwashing composition of the present invention. It is further understood that while general attributes of each of the above categories of materials may differ, there may be some common attributes and any given material may serve multiple purposes within two or more of such categories of materials. In certain embodiments, such additives are selected for compatibility with the bioactive glass and with other ingredients of the composition.

A. Surfactants

Surfactants suitable for use in the invention include but are not limited to: anionic surfactants, nonionic surfactants, cationic surfactants, amphoteric surfactants, ampholytic surfactants, zwitterionic surfactants, and mixtures thereof, as known to one of ordinary skill in the art. Suitable surfactants may be added in any suitable amount or form, may optionally be in a surfactant system, and may be added to provide any desired properties including, but not limited to, cleaning and/or foaming properties. Suitable surfactants may include anionic, cationic, nonionic and amphoteric surfactants.

In one embodiment, a composition of the present invention includes at least one surfactant. In one embodiment, a composition including at least one surfactant includes sodium lauryl sulfate. In one embodiment, a composition includes sodium lauryl sulfate in an amount from 0.5 wt. % to 10 wt. %. In one embodiment, a composition includes sodium lauryl sulfate in an amount from 1 wt. % to 5 wt. %. In one embodiment, a composition includes sodium lauryl sulfate in an amount from 1.5 wt. % to 2 wt. %.

In one embodiment, a dentifrice composition of the invention including at least one surfactant includes a poloxamer. In one embodiment, a composition including a poloxamer includes an ethylene oxide/propylene oxide copolymer. In one embodiment, a composition including a poloxamer includes an ethylene oxide/propylene oxide copolymer in an amount from 1.0 wt. % to 45.0 wt. %. In one embodiment, a composition including a poloxamer includes an ethylene oxide/propylene oxide copolymer in an amount from 5.0 wt. % to 35.0 wt. %. In one embodiment, a composition including a poloxamer includes an ethylene oxide/propylene oxide copolymer in an amount from 10.0 wt. % to 25.0 wt. %.

B. Tartar Control Agent

In some embodiments, compositions of the invention may optionally comprise a tartar control (anti-calculus) agent formulated to not interfere with the efficacy of the bioactive glass and/or potassium salts described in detail herein. Tartar control agents among those useful herein include salts of any of these agents, for example their alkali metal and ammonium salts: phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclo-pentane-2,3-diphosphonic acid, ethane-1-hydroxy-1,1-diphosphonic acid (EHDP) and ethane-1-amino-1,1-diphosphonate, phosphonoalkane carboxylic acids and. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof.

C. Fluoride Sources

Fluoride sources suitable for use in the invention may include any orally acceptable particulated fluoride-ion containing agent formulated to not interfere with the efficacy of the bioactive glass, and that may be useful, for example, as an anti-caries agent. Suitable fluorine sources may include, but are not limited to: ionic fluorides including alkali metal fluorides; amine fluorides such as olaflur (N'-octadecyltrimethylendiamine-N,N,N'-tris(2-ethanol)-dihydrofluoride); stannous fluoride; indium fluoride; and ionic monofluorophosphates including alkali metal monofluorophosphates such as potassium, sodium and ammonium fluorides and monofluorophosphates; and mixtures thereof.

In one embodiment, a dentifrice composition of the invention further includes a fluorine source. In one embodiment, a composition further includes a fluoride salt. In one embodiment, a composition further including a fluoride salt includes sodium monofluorophosphate. In one embodiment, calcium glycerophosphate, which has been shown to enhance the activity of ionic monofluorophosphates, may be optionally added when the fluoride source is an ionic monofluorophosphate. In one embodiment, a composition may include a fluorine source providing between 100 and 3000 ppm of fluoride. In one embodiment, a composition may include a fluorine source providing between 500 and 2000 ppm of fluoride.

D. Whitening Agents

Whitening agents suitable for use in the invention may include any therapeutically effective agent suitable for use in an oral cavity. Suitable whitening agents include, but are not limited to: titanium dioxide, hydrogen peroxide, sodium tripolyphosphate, and the like. In one embodiment, a dentifrice composition of the present invention further includes a whitening agent. In one embodiment, a composition of the present invention further includes titanium dioxide. In one embodiment, titanium dioxide may be included at appropriate levels.

E. Abrasives

Abrasives suitable for use in the invention may include any orally acceptable particulated agent formulated to not interfere with the efficacy of the bioactive glass. Suitable abrasives for use in the present invention may include, but are not limited to: silica, zinc orthophosphate, sodium bicarbonate (baking soda), plastic particles, alumina, hydrated alumina, calcium carbonate, calcium pyrophosphate, and mixtures thereof. The silica abrasive may be a natural amorphous silica including diatomaceous earth; or a synthetic amorphous silica such as a precipitated silica; or a silica gel, such as a silica xerogel; or mixtures thereof.

Generally, an amount of abrasive suitable for use in the dentifrice composition of the invention will be empirically determined to provide an acceptable level of cleaning and polishing, in accordance with the techniques well known in the art. In one embodiment, a dentifrice composition of the present invention includes an abrasive. In one embodiment, a composition includes a silica abrasive. In one embodiment, a silica abrasive is present in an amount of from 1 wt. % to 30 wt. %. In one embodiment, a silica abrasive is present in an amount of from 5 wt. % to 15 wt. %. In one embodiment, a silica abrasive is present in an amount of from 7 wt. % to 10 wt. %.

F. Mouth-Feel Agents

Mouth-feel agents suitable for use in the present invention may include any orally acceptable materials imparting a desirable texture or other feeling during use of the dentifrice composition, in any form or amount. Suitable mouth-feel agents may include, but are not limited to: dispersed flavorants, sweeteners, saliva-stimulating agents, and the like.

Flavorants among those useful herein include any material or mixture of materials operable to enhance the taste of the composition. Any orally acceptable natural or synthetic flavorant can be used, such as flavoring oils, flavoring aldehydes, esters, alcohols, similar materials, and combinations thereof. Flavorants include vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants, and mixtures thereof. Also encompassed within flavorants herein are ingredients that provide fragrance and/or other sensory effect in the mouth, including cooling or warming effects. Such ingredients include menthol, menthyl acetate, menthyl lactate, camphor, eucalyptus oil, eucalyptol, anethole, eugenol, cassia, oxanone, alpha-irisone, propenyl guaiethol, thymol, linalool, benzaldehyde, cinnamaldehyde, N-ethyl-p-menthan-3-carboxamine, N,2,3-trimethyl-2-isopropylbutanamide, 3-1-menthoxypropane-1,2-diol, cinnamaldehyde glycerol acetal (CGA), methone glycerol acetal (MGA), and mixtures thereof. One or more flavorants are optionally present in a total amount of 0.01% to 5%, optionally in various embodiments from 0.05 to 2%, from 0.1% to 2.5%, and from 0.1 to 0.5%.

Sweeteners among those useful herein include orally acceptable natural or artificial, nutritive or non-nutritive sweeteners. Such sweeteners include dextrose, polydextrose, sucrose, maltose, dextrin, dried invert sugar, mannose, xylose, ribose, fructose, levulose, galactose, corn syrup (including high fructose corn syrup and corn syrup solids), partially hydrolyzed starch, hydrogenated starch hydrolysate, sorbitol, mannitol, xylitol, maltitol, isomalt, aspartame, neotame, saccharin and salts thereof, sucralose, dipeptide-based intense sweeteners, cyclamates, dihydrochalcones, and mixtures thereof. One or more sweeteners are optionally present in a total amount depending strongly on the particular sweetener(s) selected, but typically at levels of from 0.005% to 5%, optionally from 0.01% to 1%.

The compositions of the present invention may optionally comprise a saliva stimulating agent formulated to not interfere with the efficacy of the bioactive glass and/or potassium salts described in detail herein and useful, for example, in amelioration of dry mouth. One or more saliva stimulating agents are optionally present in saliva stimulating effective total amount.

G. Occlusion Agents

Occlusion agents of the invention include, but are not limited to, bioactive glass, arginine/calcium carbonate, arginine bicarbonate/calcium carbonate, and small particle silica or combinations. As used herein, the term "occlusion agent" refers to any agent that aids in remineralization of the teeth or a tooth surface or agents that deposit compounds on and in the tooth surface and when applied to dental tissue prevent and/or repair dental weaknesses. For example, bioactive glass such as amorphous calcium compounds including amorphous calcium phosphate, amorphous calcium phosphate fluoride and amorphous calcium carbonate phosphate for use in remineralizing teeth. The occlusion agents of the invention when applied to dental tissue prevent and/or repair dental weaknesses 1. Bioactive Glasses The compositions of the invention generally include one or more bio-acceptable, bioactive glasses.

Suitable bioacceptable and bioactive glasses for use in the invention include, but are not limited to, an inorganic glass material capable of forming a layer of hydroxycarbonate apatite in accordance with the present invention. In one embodiment, the dentifrice composition of the present invention includes a bioactive and bioacceptable glass. In one embodiment, the composition includes calcium sodium phosphosilicate. In one embodiment, the composition includes calcium sodium phosphosilicate in an amount from 1.0 wt. % to 20 wt. %. In one embodiment, the composition includes calcium sodium phosphosilicate in an amount from 5.0 wt. % to 15 wt. %. In one embodiment, the composition includes calcium sodium phosphosilicate in an amount of 10 wt. %.

Suitable bioacceptable and bioactive glasses may have compositions including: from 40 wt. % to 86 wt. % of silicon dioxide ($SiO_2$); from 0 wt. % to 35 wt. % of sodium oxide ($Na_2O$); from 4 wt. % to 46 wt. % of calcium oxide (CaO); and from 1 wt. % to 15 wt. % of phosphorus oxide ($P_2O_5$). Preferably, the bioacceptable and bioactive glass includes: from 40 wt. % to 60 wt. % of silicon dioxide ($SiO_2$); from 10 wt. % to 30 wt. % of sodium oxide ($Na_2O$); from 10 wt. % to 30 wt. % of calcium oxide (CaO); and from 2 wt. % to 8 wt. % of phosphorus oxide ($P_2O_5$). The oxides may be present as solid solutions or mixed oxides, or as mixtures of oxides. Exemplary bioacceptable and bioactive glass suitable for use in the present invention include NovaMin®, which has a composition including 45 wt. % of silicon dioxide, 24.5 wt. % of sodium oxide, 6 wt. % of phosphorus oxide, and 24.5 wt. % of calcium oxide.

In one embodiment, the composition of suitable bioacceptable and bioactive glass may also include: $CaF_2$, $B_2O_3$, $Al_2O_3$, MgO and $K_2O$, in addition to silicon, sodium, phosphorus and calcium oxides. In certain embodiments, the range of $CaF_2$ is from 0 wt. % to 25 wt. %. The preferred range for $B_2O_3$ is from 0 wt. % to 10 wt. %. The preferred range for $Al_2O_3$ is from 0 wt. % to 4 wt. %. The preferred range for MgO is from 0 wt. % to 5 wt. %. The preferred range for $K_2O$ is from 0 wt. % to 8 wt. %.

An "effective" amount of the bio-acceptable and bioactive glass is an amount that is sufficient to have the desired therapeutic or prophylactic effect in the human or lower animal subject to whom the active is administered, without undue adverse side effects (such as toxicity, irritation, or allergic response), commensurate with a reasonable benefit/risk ratio when used in the manner of this invention. The specific effective amount will vary with such factors as the particular condition being treated, the physical condition of the subject, the nature of concurrent therapy (if any), the specific active used, the specific dosage form, the carrier employed, and the desired dosage regimen.

The bioactive glasses of the invention provide an efficacious material for interaction with the tooth structure. A biocompatible glass in accordance with the invention is one that does not trigger an adverse immune response.

In accordance with the invention, it has been found that bioactive glasses of specified particle sizes are particularly useful in treating the above-mentioned conditions. Specifically, surprising results are obtained by the compositions of the invention where small and very small particles are combined. In certain embodiments, for example, the bioactive glass portion of the compositions include small particles that are capable of bonding with tooth structure (e.g., less than 90 microns) as well smaller particles (e.g., less than 10) are used in combination, the larger of these particles adhere to tooth structure and act as ionic reservoirs while the smaller are capable of entering and lodging inside of various tooth structure surface irregularities.

In one embodiment, bioacceptable and bioactive glass suitable for use in the present invention is particulate, non-interlinked bioactive glass. In one embodiment, the glass has a particle size range of less than 90 µm. In one embodiment, the glass has a particle size range of less than 70 µm. In one embodiment, the glass has a particle size range of less than 50 µm. In one embodiment, the glass has a particle size range of less than 40 µm. In one embodiment, the glass has a particle size range of less than 30 µm. In one embodiment, the glass has a particle size range of less than 20 µm. In certain embodiments, the particle size of the bioactive glass portion of the compositions is less than 20, 10, 5, 4, 3, 2, 1 micron.

In certain embodiments, the larger of these particles (e.g., less than 90 microns to less than 20 microns) provide a reservoir of additional calcium and phosphorous so that the mineralization, or depositing of the calcium phosphate layer begun by the small particles (e.g., less than 20 microns to less than 1 micron) can continue. In certain embodiments of the invention, additional calcium and phosphorous can be leached to all tooth structure as well as to particles, which have become attached to the inside or at the openings of surface irregularities of tooth structure such as dentinal tubules. This in turn provides for continuation of the entire reaction and continued growth of the smaller of these particles, which have lodged inside or over the openings of such surface irregularities and can result in effectively coating or filling the surface irregularity. This excess concentration of ions of calcium and phosphorous allows reaction of the smaller of these particles to take place because the smaller particles quickly exhaust their ions because of their relatively high surface area. The larger of these particles will react and release their ions more slowly as a longer term effect. Furthermore, the larger of these particles will mechanically abrade the tooth surface opening various surface irregularities allowing small particles to enter and react with the surface irregularity.

This effect is very beneficial in a variety of applications. For example, in preventing caries or decay, the compositions of the invention are capable of penetrating into the depths of the smallest of surface irregularities and receiving a continued supply of ions from larger nearby particles so that it is able to grow after exhausting its stored ion supply. This is also very useful in sealing pits and fissures, and a much more effective and long lasting seal is obtained.

The occlusion of these tubules leads to a significant reduction in the amount of sensitivity after, for example, periodontal surgery. In certain embodiments, a mixture of particles less than two microns and larger than 45 microns in diameter are used. It has been found that this combination yields a particularly effective composition.

In certain embodiments, the bio-acceptable and bioactive glass encompasses glass compositions including the following components by weight:

| Ingred. | wt. % |
|---|---|
| $SiO_2$ | 40-60 |
| $CaO_2$ | 10-30 |
| $Na_2O$ | 10-35 |
| $P_2O_5$ | 2-8 |
| $CaF_2$ | 0-25 |
| $B_2O_3$ | 0-10 |

In certain embodiments, the following composition by weight percentage encompasses a bioactive glass:

| Ingred. | wt. % |
|---|---|
| $SiO_2$ | 40-60 |
| $CaO_2$ | 10-30 |
| $Na_2O$ | 10-35 |
| $P_2O_5$ | 2-8 |
| $CaF_2$ | 0-25 |
| $B_2O_3$ | 0-10 |
| $K_2O$ | 0-8 |
| $MgO$ | 0-5 |

In various embodiments, the bioactive glass is present in the compositions in an amount of 1 wt. % to 35 wt. %, 5 wt. % to 30 wt. %, 10 wt. % to 25 wt. %, 15 wt. % to 20 wt. %, and 20 wt. %.

2. Arginine Bicarbonate/Calcium Carbonate

In certain embodiments, the occlusion agent includes an arginine bicarbonate, an amino acid complex, and particles of calcium carbonate. In certain embodiments, arginine bicarbonate/calcium carbonate is an abrasive. In certain embodiments, the arginine bicarbonate/calcium carbonate complex creates an alkaline environment to further enhance particle attachment.

In certain embodiments, the arginine-bicarbonate/calcium carbonate compositions can counter tooth mineral loss in dental caries and dentinal hypersensitivity. In other embodiments, the These arginine-bicarbonate/calcium carbonate compositions are capable of neutralizing acid production and remineralizing tooth structure.

In various embodiments, the arginine bicarbonate/calcium carbonate is present in the compositions in an amount of 1 wt. % to 35 wt. %, 5 wt. % to 30 wt. %, 10 wt. % to 25 wt. %, 15 wt. % to 20 wt. %, and 20 wt. %.

3. Small Particle Silica

In certain embodiments, the occlusion agent includes silica, in certain embodiments small particle silica. A composite restorative material which is widely used in the dental field in recent years is required to have the following properties. In certain embodiments, the small particle silica includes an ultrafine particle having an average particle size of 0.01 μm to 100 μm, 0.1 μm to 50 to 10 μm, and 5 μm, or combinations thereof.

In addition, the presence of small particle silica acted as a pH buffer to bring the formulation into the pH range accepted by ISO standards as well as offering addition occlusion benefit. In vitro retention and dentin conductance studies showed significant improvement in retention, reduction in dentinal fluid flow, and acid resistance when compared to the previously consumer and clinically tested control product In various embodiments, the small particle silica is present in the compositions in an amount of 1 wt. % to 35 wt. %, 5 wt. % to 30 wt. %, 10 wt. % to 25 wt. %, 15 wt. % to 20 wt. %, and 20 wt. %.

H. Other Actives

In some embodiments, compositions of the invention may optionally include other active materials, operable for the prevention or treatment of a condition or disorder of hard or soft tissue of the oral cavity, or the prevention or treatment of a physiological disorder or condition. In some embodiments, the active is a "systemic active" which is operable to treat or prevent a disorder that, in whole or in part, is not a disorder of the oral cavity. In some embodiments, the active is an "oral care active" operable to treat or prevent a disorder or provide a cosmetic benefit within the oral cavity (e.g., to the teeth, gingiva or other hard or soft tissue of the oral cavity). Oral care actives among those useful herein include whitening agents, anticaries agents, tartar control agents, antiplaque agents, periodontal actives, abrasives, breath freshening agents, tooth desensitizers, salivary stimulants, and combinations thereof.

In some embodiments, compositions of the invention may optionally include an antibacterial agent formulated to not interfere with the efficacy of the bioactive glass and/or potassium salts described in detail herein. Examples of antibacterial agents include, but are not limited to, triclosan, cetylpyridinium chloride, and combinations thereof.

In some embodiments, compositions of the invention include comprise a nutrient formulated to not interfere with the efficacy of the bioactive glass and/or potassium salts described in detail herein. Suitable nutrients include vitamins, minerals, amino acids, and mixtures thereof. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Nutritional supplements include amino acids (such as L-tryptophane, L-lysine, methionine, threonine, levocarnitine and L-carnitine), lipotropies (such as choline, inositol, betaine, and linoleic acid), and mixtures thereof.

In some embodiments, compositions of the invention may also contain an antistain agent. Suitable antistain agents may include, but are not limited to: carboxylic acids, amino carboxylate compounds, phosphonoacetic acid, polyvinylpyrrolidone, and the like. The antistain agent may be incorporated into the dentifrice composition or may be provided as a separate composition, for use after the dentifrice.

In some embodiments, compositions of the invention may also include an agent to enhance surface deposition/retention of the bioglass and any resulting HAP deposits including, but not limited to, Gantrez, amelogenin, milk proteins (casein), chitosan, pluracare L1220 (ethylene oxide/propylene oxide copolymer), polyox, PVP, methacrylates, shellac, arginine, and combination thereof.

III. Methods for Preparing Oral Compositions Containing Polyguanidine Compounds

The synthesis of polyguanidine compounds may be achieved through the modification of polyamines by any means known to one of ordinary skill in the art. Conversions of primary amine moieties to guanidinium groups may be accomplished at high efficiency under mild, aqueous conditions. In some embodiments, a method for preparing an oral composition of the present invention first includes selecting at least one primary amine containing polymer as illustrated in Scheme 1.

Scheme 1

In some embodiments, the primary amine containing polymer is chitosan, polyallylamine, polyvinylamine, polyaminoalkyl acrylamides, polyvinylimidazole, polyaminoalkyl (meth)acrylates, polyethyleneimine, polylysine, polyornithine compounds, and combinations thereof. In some embodiments, a method for preparing an oral composition of the present invention next includes converting the primary amine moieties on said polymer to guanidinium groups.

In some embodiments, a method for preparing an oral composition of the invention then includes titration with a counterion solution in an amount and under conditions to form a polyguanidinium counterion complex. In some embodiments, a method for preparing an oral composition of the present invention further includes titrating said polyguanidinium counterion complex with a calcium source in an amount and under conditions to form a calcium polyguanidinium counterion complex.

IV. Methods for Preventing or Treating Periodontal Disease and Caries

The invention also encompasses methods for preventing or treating periodontal disease and caries, which include delivering a therapeutically effective amount of an oral composition containing a polyguanidine compound into the oral cavity. As used herein, a therapeutically effective amount of oral composition as defined by the invention is a quantity of oral composition capable of preventing or treating periodontal disease and caries. In some embodiments, a therapeutically effective amount is a quantity capable of reducing or neutralizing the acids produced by the dental plaque as a result of carbohydrate metabolism. In some embodiments, a therapeutically effective amount is a quantity capable reducing demineralization of the dental enamel, dentine and cementum by providing calcium to suppress solubilization of the tooth by mass action or by favoring remineralization. In some embodiments, an oral composition of the present invention may be applied orally without decalcifying or otherwise damaging dental enamel.

In some embodiments, a method of targeting an active ingredient to oral epithelial tissues includes delivering a therapeutically effective amount of an oral composition of the present invention into an oral cavity. In some embodiments, a method of depositing a bacteriostatic or bacteriocidal material on oral surfaces, wherein the material persists long after brushing or rinsing, includes delivering a therapeutically effective amount of an oral composition of the present invention into an oral cavity. In some embodiments, a method of retarding or preventing dental caries includes delivering a therapeutically effective amount of an oral composition of the present invention into an oral cavity. In some embodiments, a method of treating or preventing dentinal sensitivity includes delivering a therapeutically effective amount of an oral composition of the present invention into an oral cavity.

In another aspect, a method of treating, reducing or preventing dentinal sensitivity includes delivering a therapeutically effective amount of an oral composition of the present invention into an oral cavity, such that the composition contacts the surface of a tooth in a way that introduces a portion of the composition to the opening of a dentinal tubule. In an embodiment, a portion of the composition enters the dentinal tubule, wherein the composition which has entered into the tubule effectively plugs (i.e., "occludes") the tubule such that passage of certain substances, minerals, ions, compounds, and the like is either inhibited or enhanced, resulting in desensitization of the tooth. In some embodiments, a method of plugging dentinal tubules includes delivering a therapeutically effective amount of an oral composition of the present invention into an oral cavity. In some embodiments, a method of treating a carious lesion includes delivering a therapeutically effective amount of an oral composition of the present invention into an oral cavity. In some embodiments, a method of calcifying an exposed tooth pulp includes delivering a therapeutically effective amount of an oral composition of the present invention into an oral cavity. In some embodiments, a method of calcifying the base or all of a pit or fissure in a tooth includes delivering a therapeutically effective amount of an oral composition of the present invention into an oral cavity.

EXAMPLES

Example 1

Single-Tube Toothpaste Product Including Occlusion Agent(s) and Potassium Salt(s) that Offers Superior Tooth Sensitivity Relief An illustrative embodiment of the invention encompasses a single tube toothpaste product including one or more occlusion agents and one or more potassium salts. In one illustrative embodiment, to deliver faster relief, a single tube technology that combines rapid occlusion agents, for example, a bioactive and bio-acceptable glass (e.g., Novamin® (calcium sodium phosphosilicate—$CaNaO_6PSi$, also expressed as a composition including 45 wt. % of silicon dioxide, 24.5 wt. % of sodium oxide, 6 wt. % of phosphorus oxide and 24.5 wt. % of calcium oxide) with potassium is made. The non-aqueous bioactive and bio-acceptable glass formulations with potassium were found to provide significant in vitro occlusion.

In another illustrative embodiment, the bioactive and bio-acceptable glass (e.g., Novamin) formula is surprising found to possess additional occlusion benefit by adding commercially available small particle silica (e.g., Sorbosil AC-43).

Figure 1:
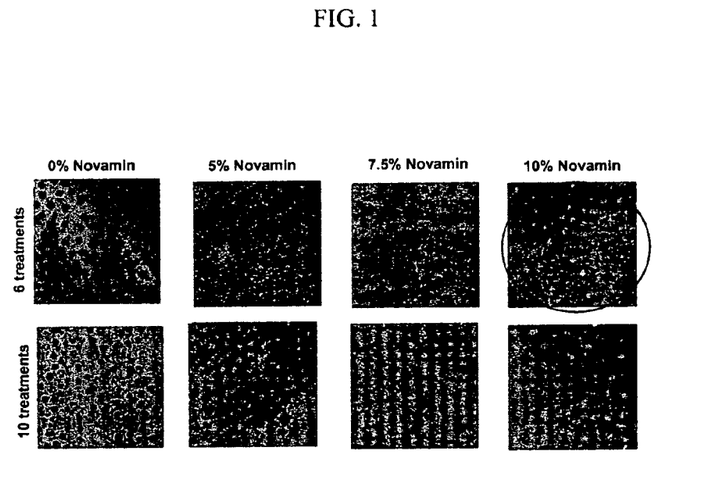
FIG. 1 is a series of images depicting the occlusion of dentinal tubules using compositions disclosed herein.

An in vitro dose response study was performed to determine the optimal bioactive and bio-acceptable glass (e.g., Novamin) level for rapid occlusion. Products with the bioactive and bio-acceptable glass (e.g., Novamin) at 5%, 7.5% and 10% were prepared. Products were evaluated by confocal microscopy after 6 and 10 brushings. After six treatments, the 10% bioactive and bio-acceptable glass (e.g., Novamin) formula showed significant occlusion while all bioactive and bio-acceptable glass (e.g., Novamin) levels provided significant occlusion after 10 treatments. See FIG. 1.

To boost the 5% bioactive and bio-acceptable glass (e.g., Novamin) occlusion at six treatments, the effect of addition of silica (e.g., Ineos AC43 silica) was studied in vitro. As shown in the confocal microscopy images in FIG. 1, the addition of 9% silica (e.g., Ineos AC43 silica) significantly improved occlusion at six treatments.

Figure 2:
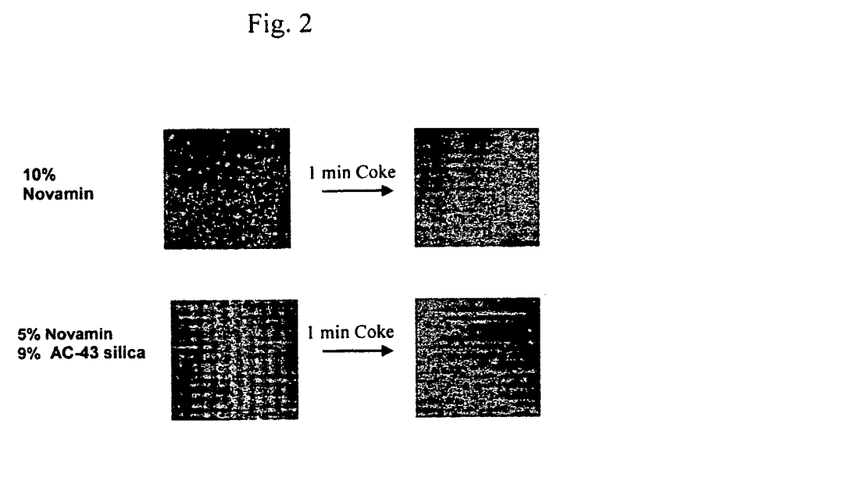
FIG. 2 is a series of images depicting the acid resistance of dentinal surfaces after treatment with compositions disclosed herein.

The acid resistance of the two leading systems was evaluated in vitro. The 6-treatment dentin disks were soaked for 1 minute in Coke Classic. Images are shown in FIG. 2. Both systems showed significant resistance to acid challenge.

To add body and prevent separation, various gums were added to the non-aqueous glycerin based formulas. In certain embodiments, carboxymethylcellulose provided the best overall mouthfeel. Carbopol provided body, but in certain embodiments imparted a sticky feel. The formulas were optimized. All lead formulas were stabile at 4 weeks at 40° C.

10% Novamin/20% Pluraflo/CMC (no KCl)
10% Novamin/3.75% KCL/CMC
5% Novamin/3.75% KCL/9% AC43/CMC Example 2

Figure 3:
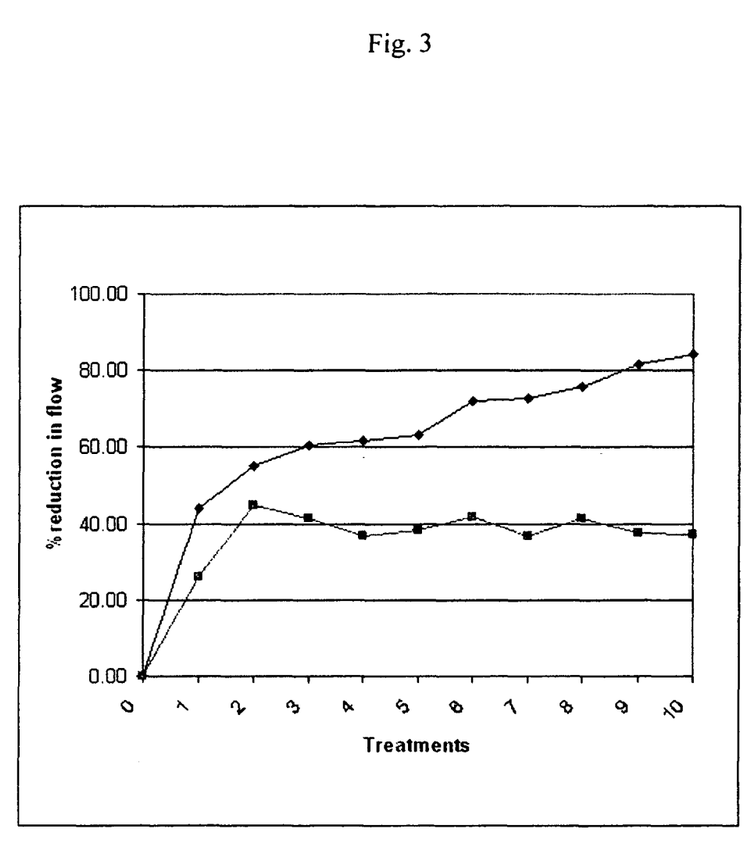
FIG. 3 is a graph depicting the comparison between dentinal conductance measured for treatment with a control composition versus a composition as disclosed herein. The top line represents the bioactive glass-containing samples and the bottom line represents the control.

Illustrated below in Table 1 is conductance data with 10% Novamin toothpaste vs. conventional non-occlusion silica toothpaste control and confocal laser microscopy images showing Novamin dose response and boosting effect of AC43 silica. A graphical depiction of the results is shown in FIG. 3.

TABLE 1

Conductance measurements after treatment with compositions disclosed herein.
Average Conductance

| Treatments | % reduction Novamin 10% | stdev | % reduction Control | stdev |
|---|---|---|---|---|
| 0 | 0.00 | 0.00 | 0.00 | 0 |
| 1 | 44.03 | 28.08 | 26.05 | 16.87 |
| 2 | 55.17 | 17.74 | 44.64 | 38.75 |
| 3 | 60.63 | 15.21 | 41.19 | 34.54 |
| 4 | 61.67 | 14.19 | 36.92 | 20.45 |
| 5 | 63.33 | 13.41 | 38.35 | 16.8 |
| 6 | 71.94 | 8.19 | 41.73 | 16.54 |
| 7 | 72.95 | 9.19 | 36.63 | 16.77 |
| 8 | 76.02 | 11.07 | 41.40 | 14.13 |
| 9 | 81.57 | 11.90 | 37.63 | 12.44 |
| 10 | 84.30 | 11.21 | 37.17 | 15.99 |

The invention is not to be limited in scope by the specific embodiments disclosed in the examples, which are intended as illustrations of a few aspects of the invention, and any embodiments, which are functionally equivalent, are within the scope of this invention. Indeed, various modifications of the invention in addition to those shown and described herein will become apparent to those skilled in the art and are intended to fall within the appended claims.

For any references that have been cited, the entire disclosures of which are incorporated herein by reference.

What is claimed is:

1. An oral composition, comprising:
  a. a polyguanidine compound of Formula (I):

wherein:
X denotes an orally acceptable counterion;
Z is CH or N;
$R_1$, $R_2$, and $R_3$ are each independently a hydrogen or a linear or branched, saturated or unsaturated, optionally hydroxylated $C_1$ to $C_{16}$ alkyl radical;
A denotes a linear or branched, saturated or unsaturated, optionally hydroxylated $C_1$ to $C_{16}$ alkyl radical; or A denotes a linear or branched, saturated or unsaturated, $C_1$ to $C_{16}$ alkylene radical optionally substituted with at least one radical selected from the group consisting of: a hydroxyl, carboxyl, or carboxylate radical or a halogen; the alkylene radical optionally containing at least one function group selected from the group consisting of: an amine, ether, thioether, ester, amide, carbamate, urea, $C_6$ aryl or $C_3$ to $C_8$ cyclanyl ring optionally substituted with a $C_1$-$C_8$ alkyl, hydroxyl or halogen; or A denotes one or more $C_6$ or $C_7$ aryl or $C_5$ to $C_7$ cyclanyl rings unsubstituted or substituted with a $C_1$-$C_8$ alkyl, a hydroxyl group or a halogen; or A denotes a $C_{10}$ to $C_{14}$ polyaryl or $C_6$ to $C_{10}$ polycyclanyl chain, which may be interrupted with at least one function group selected from the group consisting of: a $C_1$ to $C_8$ alkylene radical, amine, amide, ether, thioether, hydrogen atom, carbamate or urea; and
n denotes an integer between 2 and 5,000;
  b. an orally acceptable carrier;
  c. a bioacceptable glass composition comprising 40-60% $SiO_2$, 10-30% $CaO_2$, 10-35% $Na_2O$, 2-8% $P_2O_5$, 0-25% $CaF_2$, and 0-10% $B_2O_3$; and
  d. a small particle silica having an average particle size of 0.01 μm-10 μm.

2. The composition of claim 1, wherein said counterion is bicarbonate ($HCO_3^-$).

3. The composition of claim 1, further comprising a calcium salt.

4. The composition of claim 3, wherein said calcium salt is selected from the group consisting of: calcium carbonate, monocalcium phosphate, dicalcium phosphate, tricalcium phosphate, calcium fluoride, calcium monofluorophosphate, sodium calcium pyrophosphate, calcium laurate, calcium palmitate, and combinations thereof.

5. The composition of claim 4, wherein said calcium salt is calcium carbonate.

6. The composition of claim 1, further comprising a phosphorous source.

7. The composition of claim 6, wherein said phosphorous source is a phytate or phytic acid selected from the group consisting of: inositol triphosphate (IP3), inositol tetraphosphate (IP4), inositol pentaphosphate (IP5), inositol hexakisphosphate (IP6), and combinations thereof.

8. The composition of claim 1, wherein the oral composition is selected from the group consisting of: a dental care product, a food product, and chewing gum.

9. The composition of claim 2, further comprising a calcium salt.

10. The composition of claim 9, wherein the bioacceptable glass composition has the formula $CaNaO_6PSi$.

11. The composition of claim 10, further comprising a phosphorus source.

12. The composition of claim 1, wherein the polyguanidine compound of Formula (I) is a compound selected from the group consisting of:

,

,

, and

.

13. The composition of claim 12, further comprising a calcium salt.

14. The composition of claim 13, wherein the bioacceptable glass composition has the formula $CaNaO_6PSi$.

15. The composition of claim 14, further comprising a phosphorus source.

16. The composition of claim 1, further comprising a potassium salt.

17. The composition of claim 14, further comprising a potassium salt.

* * * * *